US010656092B2

(12) United States Patent
Ozaki et al.

(10) Patent No.: US 10,656,092 B2
(45) Date of Patent: May 19, 2020

(54) BIOLOGICAL MATERIAL QUANTIFYING METHOD, IMAGE PROCESSING DEVICE, PATHOLOGICAL DIAGNOSIS SUPPORT SYSTEM AND RECORDING MEDIUM

(71) Applicant: Konica Minolta, Inc., Chiyoda-ku, Tokyo (JP)

(72) Inventors: Yuichi Ozaki, Hino (JP); Kensaku Takanashi, Hino (JP); Daisuke Tomioka, Nishitokyo (JP)

(73) Assignee: Konica Minolta, Inc., Chiyoda-ku, Tokyo (JP)

( * ) Notice: Subject to any disclaimer, the term of this patent is extended or adjusted under 35 U.S.C. 154(b) by 9 days.

(21) Appl. No.: 16/315,249

(22) PCT Filed: Jun. 2, 2017

(86) PCT No.: PCT/JP2017/020646
§ 371 (c)(1),
(2) Date: Jan. 4, 2019

(87) PCT Pub. No.: WO2018/008309
PCT Pub. Date: Jan. 11, 2018

(65) Prior Publication Data
US 2019/0162667 A1 May 30, 2019

(30) Foreign Application Priority Data
Jul. 5, 2016 (JP) ................. 2016-132975

(51) Int. Cl.
*G01N 21/64* (2006.01)
*G01N 33/58* (2006.01)
(Continued)

(52) U.S. Cl.
CPC ......... *G01N 21/6458* (2013.01); *G01N 21/64* (2013.01); *G01N 33/54313* (2013.01);
(Continued)

(58) Field of Classification Search
CPC .. G01N 21/64; G01N 21/645; G01N 21/6456; G01N 21/6458; G01N 21/6486;
(Continued)

(56) References Cited

U.S. PATENT DOCUMENTS

| 5,928,627 A * | 7/1999 | Kiefer | A61K 49/0021 424/9.6 |
| 7,426,026 B2 * | 9/2008 | Matsumoto | G01N 21/6428 250/459.1 |

(Continued)

FOREIGN PATENT DOCUMENTS

| WO | WO 2012/029342 A1 | 3/2012 |
| WO | WO 2013/146841 A1 | 10/2013 |

OTHER PUBLICATIONS

International Search Report issued in Parent Application No. PCT/JP2017/020646, dated Sep. 5, 2017.
(Continued)

*Primary Examiner* — Thomas R Artman
(74) *Attorney, Agent, or Firm* — BakerHostetler (57) ABSTRACT

A method of quantifying a specific biological material in a specimen stained using fluorescent dye accumulating particles capable of binding to the material includes: inputting a first fluorescence image obtained by capturing an image of the specimen; extracting a certain region from the first fluorescence image and calculating a first luminance integrated value by integrating luminance values of the certain region; and calculating the number of the particles included in the certain region from the first luminance integrated value and an average luminance value per fluorescent dye accumulating particle, wherein the average luminance value is calculated from a distribution of second luminance integrated values obtained by integrating luminance values for individual bright spot regions, which indicate emission of light by the fluorescent dye accumulating particles, in a (Continued)

second fluorescence image obtained by capturing an image of a preparation onto which the fluorescent dye accumulating particles are dispersed without agglomerating.

17 Claims, 7 Drawing Sheets (51) Int. Cl.
G06T 1/00 (2006.01)
G01N 33/543 (2006.01)
(52) U.S. Cl.
CPC ..... *G01N 33/54346* (2013.01); *G01N 33/582* (2013.01); *G01N 33/585* (2013.01); *G01N 33/587* (2013.01); *G06T 1/00* (2013.01); *G06T 1/0007* (2013.01)
(58) Field of Classification Search
CPC ............ G01N 23/223; G01N 23/076; G01N 23/0766; G01N 23/401; G01N 23/612; G01N 23/6126; G01N 33/58; G01N 33/582; G01N 33/585; G01N 33/587
See application file for complete search history.

(56) References Cited

U.S. PATENT DOCUMENTS

| | | | | |
|---|---|---|---|---|
| 7,582,415 | B2 * | 9/2009 | Straus | B82Y 20/00 435/4 |
| 9,090,462 | B2 * | 7/2015 | Straus | G01N 33/56916 |
| 9,290,382 | B2 * | 3/2016 | Straus | G01N 33/56916 |
| 9,972,087 | B2 * | 5/2018 | Isoda | G06T 7/90 |
| 10,080,484 | B2 * | 9/2018 | Yang | G01J 3/28 |
| 10,234,391 | B2 * | 3/2019 | Gouda | G01N 21/6486 |
| 10,309,900 | B1 * | 6/2019 | Gouda | G01N 21/6486 |
| 2003/0082516 | A1 * | 5/2003 | Straus | G01N 33/56916 435/4 |
| 2007/0121099 | A1 * | 5/2007 | Matsumoto | G01N 21/6428 356/72 |
| 2009/0315987 | A1 * | 12/2009 | Straus | G01N 33/56916 348/79 |
| 2010/0248281 | A1 * | 9/2010 | Straus | G01N 33/56916 435/19 |
| 2011/0081664 | A1 * | 4/2011 | Forbes | C12M 23/16 435/7.23 |
| 2012/0007001 | A1 * | 1/2012 | Ishihara | A61B 1/00057 250/459.1 |
| 2013/0157895 | A1 * | 6/2013 | Aimiya | G01N 21/6428 506/9 |
| 2013/0177921 | A1 * | 7/2013 | Chastain | C12Q 1/68 435/6.19 |
| 2013/0203613 | A1 * | 8/2013 | Burmeister | B01L 3/502715 506/9 |
| 2013/0230866 | A1 * | 9/2013 | Miyashita | G01N 21/6428 435/7.23 |
| 2015/0216398 | A1 * | 8/2015 | Yang | A61B 1/043 600/109 |
| 2015/0314019 | A1 * | 11/2015 | Sokolov | A61K 49/0052 424/9.6 |
| 2017/0029864 | A1 * | 2/2017 | Straus | G01N 33/56916 |
| 2017/0186156 | A1 * | 6/2017 | Isoda | G06T 7/90 |
| 2018/0024059 | A1 * | 1/2018 | Gouda | G01N 21/6486 382/133 |
| 2019/0154582 | A1 * | 5/2019 | Gouda | G01N 21/6486 |

OTHER PUBLICATIONS

International Preliminary Report on Patentability issued in Parent Application No. PCT/2017/020646, dated Jan. 8, 2019.

* cited by examiner

BIOLOGICAL MATERIAL QUANTIFYING METHOD, IMAGE PROCESSING DEVICE, PATHOLOGICAL DIAGNOSIS SUPPORT SYSTEM AND RECORDING MEDIUM

The present U.S. Patent Application is U.S. National Phase Application under 35 U.S.C. 371 of International Application No. PCT/JP2017/020646 filed on Jun. 2, 2017. This application claims a priority under the Paris Convention of Japanese Patent Application No. 2016-132975 filed on Jul. 5, 2016, the entire disclosure of which is incorporated herein by reference in its entirety.

TECHNICAL FIELD

The present invention relates to a biological material quantifying method, an image processing device, a pathological diagnosis support system and program, and particularly relates to image processing used for pathological diagnosis.

BACKGROUND ART

In pathological diagnosis, quantifying an expression level of a biological material that is overexpressing in a tissue section can be very important information in predicting prognosis or determining a subsequent treatment plan. In such quantification of a biological material, an expression level of a specific biological material in a region of interest, which is a region to be analyzed that has been set in a tissue section, is analyzed; therefore, development of approaches has been desired that are capable of accurately performing the quantification of the biological material and extraction of the region of interest.

Accordingly, Patent Literature 1, for example, describes a method in which pixels with maximal luminance values are extracted as fluorescent bright spots using Top-hat transform or the like from a fluorescence image obtained by capturing an image of a tissue specimen in which a specific protein has been stained using fluorescent material accumulating particles and an expression level of the specific protein in the image is analyzed. According to the method described in Patent Literature 1, the fluorescent material accumulating particles have a high luminance per particle and in the fluorescence image, the biological material that has been stained fluorescently is observed in the form of dots; thus, the quantification is easy.

In addition, Patent Literature 2, for example, describes a method of calculating the number of particles included in each bright spot based on an average luminance value per fluorescent material accumulating particle. In the method described in Patent Literature 2, a similar fluorescence image as Patent Literature 1 is used to calculate luminance values of fluorescence emission bright spots, and the mode of the luminance values is used as an average luminance value per fluorescent material accumulating particle.

CITATION LIST

Patent Literature

Patent Literature 1: International Publication No. WO 2013/146841
Patent Literature 2: International Publication No. WO 2012/029342

SUMMARY OF INVENTION

Technical Problem

Figure 8A:
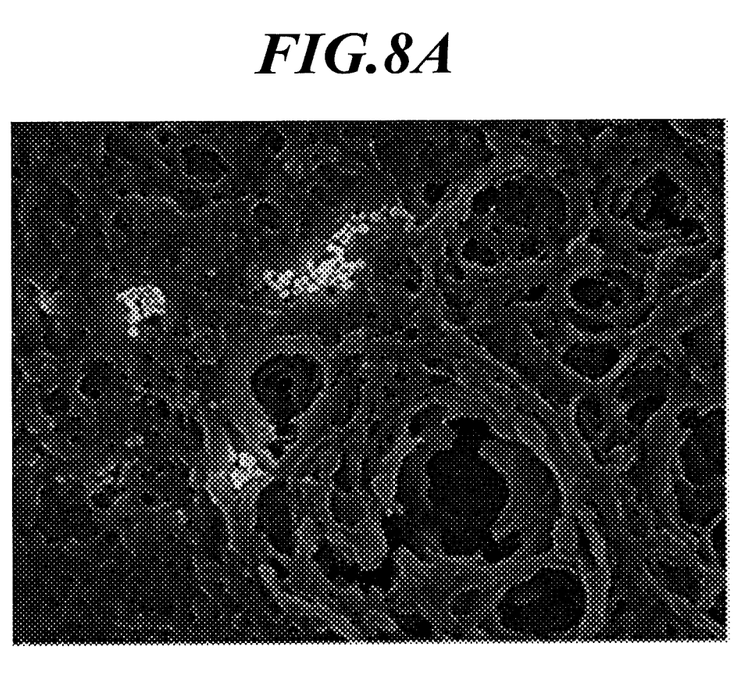
FIG. 8A is an example of a SEM image of agglomerated, multiple fluorescent dye accumulating particles.
Figure 8B:
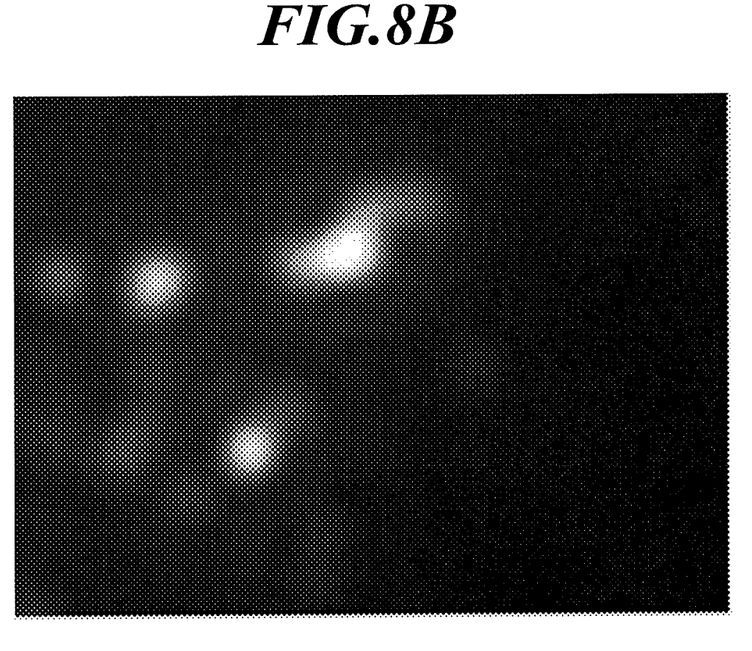
FIG. 8B is an example of a fluorescence image of the agglomerated, multiple fluorescent dye accumulating particles in FIG. 8A.

However, in the method described in Patent Literature 1, when a specific protein is expressed at a high density, multiple fluorescent dye accumulating particles, which have become like a cluster shape as shown in the SEM image of FIG. 8A, are measured as a single bright spot based on a fluorescence image, such as the one in FIG. 8B. As a result, there has been a problem that the expression level of the specific protein is calculated as less than actual.

Moreover, in the method described in Patent Literature 2, when a specific protein is expressed at a high density and many fluorescent material accumulating particles with a cluster shape are present, an error is likely to occur that a luminance value to be the mode is calculated as a greater value than the actual average luminance value per particle. In addition, luminance values measured from a fluorescence image obtained by capturing an image of a tissue specimen include, other than fluorescence emitted by the fluorescent material accumulating particles, a variety of background noises, such as autofluorescence of cells; thus, errors are likely to occur in the result. In the technique described in Patent Literature 2, there has been a problem that it is difficult to perform an accurate quantification while compensating such errors.

The main object of the present invention is to provide a biological material quantifying method, an image processing device, a pathological diagnosis support system and program with which a specific biological material in a tissue specimen can be quantified accurately and simply by using fluorescent dye accumulating particles bound to the biological material.

The above described problems with relation to the present invention are solved by the following means.

Solution to Problem

To achieve at least one of the above-mentioned objects, according to an aspect of the present invention a biological material quantifying method of quantifying a specific biological material in a specimen that has been stained using fluorescent dye accumulating particles capable of binding to the specific biological material, the biological material quantifying method including: an input step of inputting a first fluorescence image obtained by capturing an image of the specimen; a luminance calculation step of extracting a certain region from the first fluorescence image and calculating a first luminance integrated value by integrating luminance values of the certain region; and a particle count calculation step of calculating the number of the fluorescent dye accumulating particles included in the certain region from the first luminance integrated value and an average luminance value per said fluorescent dye accumulating particle, wherein the average luminance value is calculated from a distribution of second luminance integrated values obtained by integrating luminance values for individual bright spot regions, which indicate emission of light by the fluorescent dye accumulating particles, in a second fluorescence image obtained by capturing an image of a preparation onto which the fluorescent dye accumulating particles are dispersed without agglomerating.

An image processing device that quantifies a specific biological material in a specimen that has been stained using fluorescent dye accumulating particles capable of binding to the specific biological material, the image processing device including:

input means for inputting a first fluorescence image obtained by capturing an image of the specimen;

luminance calculation means for extracting a certain region from the first fluorescence image and calculating a first luminance integrated value by integrating luminance values of the certain region; and particle count calculation means for calculating the number of the fluorescent dye accumulating particles included in the certain region from the first luminance integrated value and an average luminance value per said fluorescent dye accumulating particle, wherein the average luminance value is calculated from a distribution of second luminance integrated values obtained by integrating luminance values for individual bright spot regions, which indicate emission of light by the fluorescent dye accumulating particles, in a second fluorescence image obtained by capturing an image of a preparation onto which the fluorescent dye accumulating particles are dispersed without agglomerating.

In another aspect of the present invention, a non-temporary, computer-readable recording medium may store a program causing a computer that quantifies a specific biological material in a specimen that has been stained using fluorescent dye accumulating particles capable of binding to the specific biological material to:

extract a certain region from a first fluorescence image obtained by capturing an image of the specimen; calculate a first luminance integrated value by integrating luminance values of the certain region; and calculate the number of the fluorescent dye accumulating particles included in the certain region from the first luminance integrated value and an average luminance value per said fluorescent dye accumulating particle, wherein the average luminance value is calculated from a distribution of second luminance integrated values obtained by integrating luminance values for individual bright spot regions, which indicate emission of light by the fluorescent dye accumulating particles, in a second fluorescence image obtained by capturing an image of a preparation onto which the fluorescent dye accumulating particles are dispersed without agglomerating.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DESCRIPTION OF EMBODIMENTS

Hereinafter, one or more embodiments of the present invention will be described with reference to the drawings. However, the scope of the invention is not limited to the disclosed embodiments.

Hereinafter, embodiments for carrying out the present invention will be described while referring to figures, but the present invention is not limited thereto. According to a biological material quantifying method, an image processing device, a pathological diagnosis support system and program of the present invention, a specific biological material in a tissue specimen can be quantified accurately and simply by using fluorescent dye accumulating particles bound to the biological material.

Configuration of Pathological Diagnosis Support System 100

Figure 1:
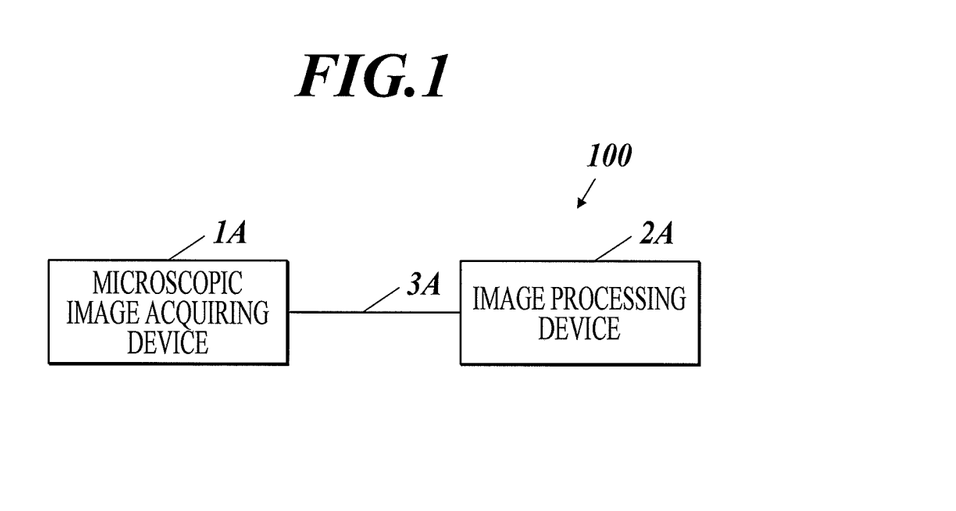
FIG. 1 shows a system configuration of a pathological diagnosis support system that uses a tissue evaluation method of the present invention.

FIG. 1 shows an example of the entire configuration of a pathological diagnosis support system 100 that uses a tissue evaluation method of the present invention. The pathological diagnosis support system 100 is a system that acquires a microscopic image of a tissue specimen that has been stained with a certain staining reagent, analyzes the acquired microscopic image, and thereby outputs a characteristic amount that quantitatively represents expression of a specific biological material in the tissue specimen to be observed.

The pathological diagnosis support system 100 is constituted by a microscopic image acquiring device 1A and an image processing device 2A, connected via an interface, such as a cable 3A, that allows data transmission and reception, as shown in FIG. 1. A connection mode between the microscopic image acquiring device 1A and the image processing device 2A is not particularly limited. For example, the microscopic image acquiring device 1A and the image processing device 2A may be connected via LAN (Local Area Network), or a configuration of connecting them in a wireless manner may be employed. Alternatively, the pathological diagnosis support system 100 may be a device in which the microscopic image acquiring device 1A and the image processing device 2A are formed in an integrated manner. Moreover, an image acquired with the use of any external device may be inputted to the image processing device via a storage, such as HDD, CD and DVD.

The microscopic image acquiring device 1A is a known optical microscope with camera that acquires a microscopic image of a tissue specimen on a slide mounted on a slide fixing stage.

The microscopic image acquiring device 1A is equipped with and constituted by irradiation means, image-forming means, image-capturing means, a communication I/F, etc. The irradiation means is constituted by a light source, filter, etc., and irradiates light to the tissue specimen on the slide mounted on the slide fixing stage. The image-forming means is constituted by an eyepiece lens, an objective lens, etc., and images transmitted light, reflected light or fluorescence emitted from the tissue specimen on the slide due to the irradiated light. The image-capturing means is a camera provided on the microscope, that is equipped with a CCD (Charge Coupled Device) sensor, etc., and that captures an image formed on the image plane by the image-forming means and generates a digital image data of the microscopic image. The communication I/F transmits the generated image data of the microscopic image to the image processing device 2A.

The image processing device 2A calculates expressing distribution of the specific biological material in the tissue specimen to be observed by analyzing the microscopic image (bright field image and fluorescence image) transmitted from the microscopic image acquiring device 1A.

Figure 2:
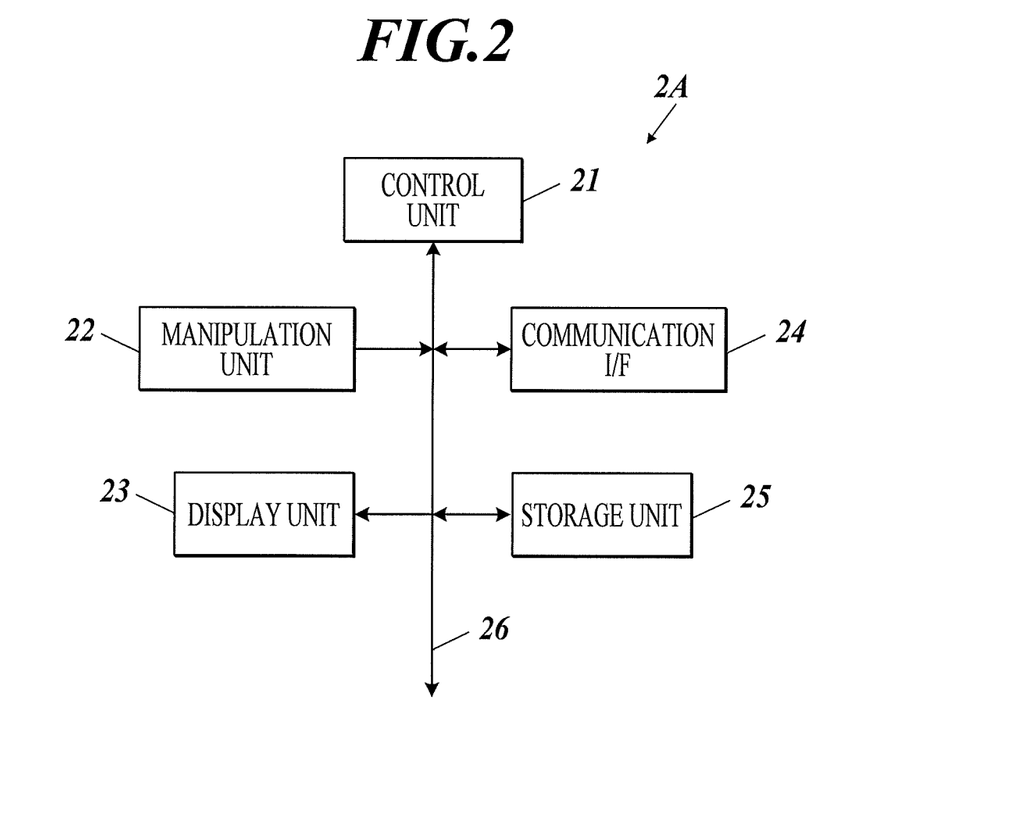
FIG. 2 is a block diagram indicating a functional configuration of the image processing device in FIG. 1.

The image processing device 2A is equipped with and constituted by a control unit 21, a manipulation unit 22, a display unit 23, a communication I/F 24, a storage unit 25, etc., and each unit is connected via a bus 26, as shown in FIG. 2.

The control unit 21 is equipped with and constituted by CPU (Central Processing Unit), RAM (Random Access Memory), etc., and exerts various processings in cooperation with various programs stored in the storage unit 25, and controls operation of the image processing device 2A integrally. For example, the control unit 21 exerts an image analysis processing in cooperation with a program stored in the storage unit 25, and implements a function as means for exerting a (first) luminance calculation step, a second luminance calculation step, an average luminance calculation step, a particle count calculation step and a calibration step.

The manipulation unit 22 is equipped with and constituted by a keyboard equipped with character input keys, numeric input keys, various function keys and the like, as well as a pointing device, such as a mouse, and outputs a press down signal for the key that is pressed down on the keyboard and a manipulation signal by the mouse to the control unit 21 as an input signal.

The display unit 23 is equipped with and constituted by a monitor, such as CRT (Cathode Ray Tube) or LCD (Liquid Crystal Display), and displays various screens according to the direction of a display signal inputted from the control unit 21. In the present embodiment, the display unit 23 functions as output means for outputting, for example, results of the image analysis.

The communication I/F 24 is an interface for performing data transmission and reception with an external instrument including the microscopic image acquiring device 1A. The communication I/F 24 functions as means for executing a (first) input step and a second input step.

The storage unit 25 is constituted by, for example, HDD (Hard Disk Drive), a semiconductor nonvolatile memory, or the like. The storage unit 25 stores various programs, various data or the like as mentioned previously.

Other than the above, the image processing device 2A may have a configuration that is equipped with a LAN adapter, a router or the like, and is connected with external instruments via a communication network, such as LAN.

Acquisition of Image from Tissue Specimen

From now, provision of a tissue specimen according to the present invention will be described in details, as well as a staining reagent and a staining method.

(1) Biological Material of Interest

A tissue specimen according to the present invention is stained with a staining reagent that includes fluorescent dye accumulating particles capable of staining a biological material of interest. The biological material of interest is a biological material that expresses in a tissue section, and is particularly a protein (antigen). Examples of a typical biological material of interest include those expressing on the cell membrane of various cancer tissues and capable of being used as a biomarker.

(2) Fluorescent Dye Accumulating Particles

Fluorescent dye accumulating particles according to the present invention are nano-sized particles that emit fluorescence in response to irradiation with excitation light and that can emit fluorescence with a sufficient strength so that each molecule of the biological material of interest is represented as a bright point.

Any emission wavelength may be used as the emission wavelength of the fluorescent dye accumulating particles, as long as it is within the sensitivity range of an image-capturing device in a fluorescence microscope. In particular, the emission wavelength is preferably 400 to 700 nm.

An average particle size of the fluorescent dye accumulating particles is not particularly limited, but when the particle size is large, it is hard for the particles to access the antigen, and when the particle size is small and the luminance value is low, the emitted fluorescence is buried in background noises (noises from the camera or autofluorescence of cells), and therefore, those with an average particle size of about 20 to 200 nm are suitable.

In addition, a coefficient of variation of the particle size is preferably 15% or less. A small variation in the particle size of the fluorescent dye accumulating particles provides an almost constant luminance value of fluorescence per particle, thereby enhancing the quantification accuracy.

The average particle size was determined by taking an electron micrograph with a scanning electron microscope (SEM), measuring cross sections of a sufficient number of particles, and determining the diameter of a circle wherein each measured value is presumed to be the area of a circle. In the present application, an arithmetic average of particle sizes of 1000 particles was set to be the average particle size. For the coefficient of variation, a value calculated from the particle size distribution of 1000 particles was used.

(2) Fluorescent Dye Accumulating Particles

The fluorescent dye accumulating particles are nano-sized particles having a configuration in which a base material of particles made of an organic or inorganic matter includes multiple fluorescent dyes therein, and/or has multiple fluorescent dyes adsorbed on its surface.

For the fluorescent dye accumulating particles, those in which the base material and the fluorescent dyes have substituents or sites that have an opposite electric charge from each other and thereby an electrostatic interaction works are suitable.

(2.1) Base Material

Among the base material, examples of the organic matter include: resins generally classified into thermosetting resins, such as melamine resins, urea resins, aniline resins, guanamine resins, phenol resins, xylene resins and furan resins; resins generally classified into thermoplastic resins, such as styrene resins, acrylic resins, acrylonitrile resins, AS resins (acrylonitrile-styrene copolymers) and ASA resins (acrylonitrile-styrene-methyl acrylate copolymers); other resins, such as polylactic acid; and polysaccharides.

Among the base material, examples of the inorganic matter include silica and glass.

(2.3) Fluorescent Dye Accumulating Particles

The fluorescent dye accumulating particles have a configuration in which fluorescent dyes are included in the base material described above, and/or are adsorbed on its surface.

Examples of the fluorescent dyes include rhodamine dye molecules, squarylium dye molecules, cyanine dye molecules, aromatic ring based dye molecules, oxazine dye molecules, carbopyronine dye molecules and pyrromethene dye molecules.

For the fluorescent dyes, Alexa Fluor (registered trademark, manufactured by Invitrogen Corporation) dye molecules, BODIPY (registered trademark, manufactured by Invitrogen Corporation) dye molecules, Cy (registered trademark, manufactured by GE Healthcare) dye molecules, HiLyte (registered trademark, manufactured by AnaSpec, Inc.) dye molecules, DyLight (registered trademark, manufactured by Thermo Fisher Scientific K.K.) dye molecules, ATTO (registered trademark, manufactured by ATTO-TEC GmbH) dye molecules, MFP (registered trademark, manufactured by MoBiTec GmbH) dye molecules, CF (registered trademark, manufactured by Biotium) dye molecules, DY (registered trademark, manufactured by Dyomics GmbH) dye molecules, CAL (registered trademark, manufactured by BioSearch Technologies, Inc.) dye molecules or the like can be used When the fluorescent dyes are included in the base material, the fluorescent dyes are just required to be dispersed within the base material, and may be chemically bound to or not bound to the base material itself.

(2.2) Quantum Dot Accumulating Particles

In the present invention, quantum dot accumulating particles may be used as the fluorescent dye accumulating particles.

The quantum dot accumulating particles have a configuration in which quantum dots are included in the base material described above, and/or are adsorbed on its surface.

For the quantum dots, semiconductor nanoparticles containing a Group II-VI compound, a Group III-V compound, or a Group IV element are used. Examples include CdSe, CdS, CdTe, ZnSe, ZnS, ZnTe, InP, InN, InAs, InGaP, GaP, GaAs, Si and Ge.

When the quantum dots are included in the base material, the quantum dots are just required to be dispersed within the base material, and may be chemically bound to or not bound to the base material itself.

(3) Staining Reagent (Antibody-Fluorescent Dye Accumulating Particle Conjugate)

The staining reagent is designed such that one fluorescent dye accumulating particle binds to one biological material of interest.

In the case of a staining reagent that is used for immunostaining (immunostaining agent), in order to improve efficiency of fluorescent labeling and to prevent time passage, which leads to degradation of the fluorescence, as much as possible, it is preferable that a composite be used in which a primary antibody and a fluorescent dye accumulating particle are indirectly linked, that is, via a bond that utilizes an antigen-antibody reaction, etc., other than a covalent bond. In order to make the staining operation easier, as the immunostaining agent, a composite can also be used in which a fluorescent dye accumulating particle is directly linked to a primary antibody or a secondary antibody.

Examples of the immunostaining agent include [primary antibody against biological material of interest as antigen] . . . [antibody against primary antibody as antigen (secondary antibody)]-[fluorescent dye accumulating particle].

The " . . . " represents a bond by an antigen-antibody reaction, and an aspect of the bond indicated by the "-" is not particularly limited and examples thereof include a covalent bond, an ionic bond, a hydrogen bond, a coordination bond, an antigen-antibody binding, a biotin-avidin reaction, physical adsorption and chemical adsorption. If necessary, a bond via a linker molecule may be used.

As the primary antibody, an antibody that specifically recognizes and binds to the biological material of interest as an antigen is used. For example, an anti-HER2 antibody or an anti-HER3 antibody is used when the biological material of interest is HER2 or HER3, respectively.

As the secondary antibody, an antibody that specifically recognizes and binds to the primary antibody as an antigen is used.

Types of animals for producing antibodies (immunized animals) are not particularly limited, and are selected from a mouse, a rat, a guinea pig, a rabbit, a goat, a sheep and the like, in the same manner as the prior art.

(4) Method of Staining Tissue Section

Hereinafter, an example of a method of staining a tissue specimen will be described with reference to the case of staining a paraffin embedded tissue section (hereinafter, may also be simply referred to as the "section"), but as the tissue specimen according to the present invention, anything selected from tissue sections, specimens acquired by needle biopsy, cultured cells or the like may be used.

(4.1) Specimen Production Step (4.1.1) Deparaffinization Processing

The section is immersed in a container containing xylene to remove paraffin. The temperature is not particularly limited, and the processing can be performed at room temperature. Preferably, the immersing time is 3 minutes or longer and 30 minutes or shorter. If necessary, xylene may also be changed during the immersion.

Next, the section is immersed in a container containing ethanol to remove xylene. The temperature is not particularly limited, and the processing can be performed at room temperature. Preferably, the immersing time is 3 minutes or longer and 30 minutes or shorter. If necessary, ethanol may also be changed during the immersion.

Next, the section is immersed in a container containing water to remove ethanol. The temperature is not particularly limited, and the processing can be performed at room temperature. Preferably, the immersing time is 3 minutes or longer and 30 minutes or shorter. If necessary, water may also be changed during the immersion.

(4.1.2) Activation Processing

In accordance with known methods, the biological material of interest is subjected to an activation processing. Conditions for the activation are not particularly defined, but as for the activation solution, a 0.01 M citrate buffer solution (pH 6.0), a 1 mM EDTA solution (pH 8.0), 5% urea, a 0.1 M Tris-hydrochloride buffer solution or the like can be used.

The activation processing is performed under a condition of pH 2.0 to 13.0 depending on the tissue section used, so that a signal is emitted and damages of the tissue do not prevent evaluation of the signal from the tissue. The activation processing is usually performed at pH 6.0 to 8.0, but is performed even at pH 3.0, for example, in the case of a special tissue section.

As for a heater, an autoclave, a microwave, a pressure cooker, a water bath or the like can be used. The temperature is not particularly limited, and the processing can be performed at the temperature of 50 to 130° C. and for the time period of 5 to 30 minutes. The processing can be performed at room temperature as well.

Subsequently, the section after the activation processing is immersed in a container containing PBS and washing is performed. The temperature is not particularly limited, and the processing can be performed at room temperature. Preferably, the immersing time is 3 minutes or longer and 30 minutes or shorter. If necessary, PBS may also be changed during the immersion.

(4.2) Immunostaining Step

In the immunostaining step, in order to stain the biological material of interest, a solution of the immunostaining agent including the fluorescent dye accumulating particles that have a site capable of directly or indirectly binding to the biological material of interest is put on the section to perform a reaction with the biological material of interest. The solution of the immunostaining agent used for the immunostaining step may be prepared in advance before this step.

Conditions for performing the immunostaining step, that is, the temperature and the immersing time upon the immersion of the tissue specimen in the solution of the immunostaining agent, can be appropriately adjusted in accordance with conventional immunostaining methods so that appropriate signals can be obtained.

The temperature is not particularly limited, and the processing can be performed at room temperature. Preferably, the reaction time is 30 minutes or longer and 24 hours or shorter.

Before performing the processing as mentioned above, it is preferable that a known blocking agent, such as BSA-containing PBS, or a surfactant, such as Tween 20, be added dropwise.

(4.3) Post-Processing Step for Specimen

After the immunostaining step, it is preferable that the tissue specimen be subjected to processings, such as fixation and dehydration, permeation, and mounting, to make the tissue specimen suitable for observation.

In the fixation and dehydration processing, the tissue specimen may be immersed in a fixation processing solution (crosslinking agent, such as formalin, paraformaldehyde, glutaraldehyde, acetone, ethanol and methanol). In the permeation processing, the tissue specimen after the fixation and dehydration processing may be immersed in a permeation solution (such as xylene). In the mounting processing, the tissue specimen after the permeation processing may be immersed in a mounting solution.

Conditions for performing these processings, such as the temperature and the immersing time upon the immersion of the tissue specimen in a certain processing solution, can be appropriately adjusted in accordance with conventional immunostaining methods so that appropriate signals can be obtained.

(4.4) Staining Step for Morphological Observation

Apart from the immunostaining step, staining for morphological observation may be performed for making it easier to observe the morphology of a cell, tissue, organ and the like in the bright field. The staining step for morphological observation can be performed according to any known methods, and may be performed before or after the immunostaining step.

For morphological observation of the tissue specimen, staining with eosin is normally used for staining cytoplasm, interstitium, various fibers, red blood cell and keratinocyte in red to dark red. In addition, staining with hematoxylin is also normally used for staining a cell nucleus, calcification portion, cartilage, bacteria and mucus in livid to light blue; a method to perform these two stainings simultaneously is known as hematoxylin-eosin staining (HE staining).

Production of Fluorescent Dye Accumulating Particle-Dispersed Preparation

Next, a fluorescent dye accumulating particle-dispersed preparation, which is used for calculating an average luminance value per fluorescent dye accumulating particle, will be described.

Hereinafter, a production step for the fluorescent dye accumulating particle-dispersed preparation will be specifically described, but any fluorescent dye accumulating particle-dispersed preparation may be used as the fluorescent dye accumulating particle-dispersed preparation of the present invention, as long as it is a specimen for microscopic observation in which the fluorescent dye accumulating particles mentioned above are dispersed while avoiding agglomeration.

[Production Method 1]

(1) Fluorescent dye accumulating particles with a given average particle diameter (for example, 150 nm) are provided.

(2) The fluorescent dye accumulating particles are diluted with PBS to produce a solution of the fluorescent dye accumulating particles with a concentration of 0.005 nM.

(3) A slide glass is provided.

(4) Onto the slide glass, 7.5 µL of the solution of the fluorescent dye accumulating particles is dripped such that the dripping area is equivalent to the area of a circle with the diameter of 5.0 mm.

(5) The slide glass is allowed to stand still for 10 minutes.

(6) The slide glass is immersed in a 300 mL beaker containing pure water and washed.

(7) The slide glass is fitted to a staining basket and washed with running water for 10 minutes.

(8) The staining basket is taken out from water and is passed through three ethanol phases for dehydration and three xylene phases for xylene replacement.

(9) The slide glass is mounted with a xylene mounting agent (marinol).

In the production method 1, it is possible to control the density of the fluorescent dye accumulating particles by changing, for example, the concentration of the solution of the fluorescent dye accumulating particles. A particle density in the fluorescent dye accumulating particle-dispersed preparation is preferably $10^6$ counts/mm$^2$ or less.

[Production Method 2: Method of Controlling Dispersion Density by Dispersing Dissolvable Particles Different from Fluorescent Dye Accumulating Particles]

(1) Fluorescent dye accumulating particles with a given average particle diameter (for example, 150 nm) are provided.

(2) The fluorescent dye accumulating particles are diluted with PBS to produce a solution of the fluorescent dye accumulating particles with a concentration of 0.005 nM.

(3) Polystyrene particles with the diameter of 200 nm (manufactured by Invitrogen Corporation) are provided.

(4) The polystyrene particles are diluted with PBS to produce a solution of the polystyrene particles with a concentration of 0.500 nM.
(5) A slide glass is provided.
(6) Onto the slide glass, 7.5 μL of the solution of the polystyrene particles is dripped such that the dripping area is equivalent to the area of a circle with the diameter of 5.0 mm.
(7) The slide glass is allowed to stand still for 10 minutes.
(8) The slide glass is immersed in a 300 mL beaker containing pure water to remove an extra solution of the polystyrene particles from the slide glass.
(9) The solution of the fluorescent dye accumulating particles provided in (2) is placed on the slide glass at the same location as the solution of the polystyrene particles.
(10) The slide glass is allowed to stand still for 10 minutes.
(11) The slide glass is immersed in a 300 mL beaker containing pure water and washed.
(12) The slide glass is fitted to a staining basket and washed with running water for 10 minutes.
(13) The staining basket is taken out from water and is passed through three ethanol phases for dehydration and three xylene phases for xylene replacement.
(14) The slide glass is mounted with a xylene mounting agent (marinol).

According to the production method 2, after the xylene replacement in (13), only fluorescent dye accumulating particles directly attaching to the slide glass are left on the slide glass. Since the polystyrene particles are dispersed onto the slide glass in (6) and therefore regions in which the slide glass is exposed are narrow and at a low density at the time of (9), a preparation onto which the fluorescent dye accumulating particles are dispersed without agglomerating can be obtained.

Note that, in the production method 2, after the solution of the fluorescent dye accumulating particles and the solution of the polystyrene particles are provided in (2) and (4), respectively, these solutions may be mixed and dripped onto the slide glass. After the dripping of the mixed solution, the processings of (10) to (14) described above are performed.

In the production method 2, it is possible to control the density of the fluorescent dye accumulating particles by changing, for example, a ratio between the concentrations of the solution of the polystyrene particles and the solution of the fluorescent dye accumulating particles.

[Production Method 3: Method of Controlling Dispersion Density by Patterned Application of Dissolvable Resin]
(1) A slide glass is provided.
(2) Onto the slide glass, a photosensitive resin that is dissolved with xylene is applied.
(3) The photosensitive resin film is exposed to light to produce a pattern with a hole diameter of 200 nm and a pitch of 1000 μm.
(4) Fluorescent dye accumulating particles with a given average particle diameter (for example, 150 nm) are provided.
(5) The fluorescent dye accumulating particles are diluted with PBS to produce a solution of the fluorescent dye accumulating particles with a concentration of 0.005 nM.
(6) To the parts on the slide glass onto which the photosensitive resin has been applied, 100 μL of the solution of the fluorescent dye accumulating particles is dripped such that the dripping area is about 100 mm$^2$.
(7) The slide glass is allowed to stand still for 10 minutes.
(8) The slide glass is immersed in a 300 mL beaker containing pure water and washed.
(9) The slide glass is fitted to a staining basket and washed with running water for 10 minutes.
(10) The staining basket is taken out from water and is passed through three ethanol phases for dehydration and three xylene phases for xylene replacement.
(11) The slide glass is mounted with a xylene mounting agent (marinol).

According to the production method 3, after the xylene replacement in (10), the photosensitive resin is dissolved and only fluorescent dye accumulating particles directly attaching to the slide glass are left on the slide glass. Accordingly, a preparation onto which the fluorescent dye accumulating particles are dispersed without agglomerating can be obtained.

In the production method 3, it is possible to control the density of the fluorescent dye accumulating particles by changing, for example, a ratio between the hole diameter of the pattern produced in (3) and the average particle size of the fluorescent dye accumulating particles.

Operation of Pathological Diagnosis Support
System 100 (Including Image Processing Method)

Hereinafter, analytical operation in the pathological diagnosis support system 100, based on the fluorescence image and the bright field image of the above mentioned tissue specimen and the preparation onto which the fluorescent dye accumulating particles are dispersed, will be described, but the image processing of the present invention is not limited to this.

At first, an operator stains a tissue specimen with a hematoxylin staining reagent and a staining reagent using fluorescent dye accumulating particles that bind to a biological material of interest. Furthermore, a fluorescent dye accumulating particle-dispersed preparation is provided, onto which fluorescent dye accumulating particles that have been produced in the same manner as the fluorescent dye accumulating particles used for staining the tissue specimen are dispersed.

Then, by using the microscopic image acquiring device 1A, a bright field image and a fluorescence image (first fluorescence image) of the tissue specimen, and a fluorescence image (second fluorescence image) of the preparation onto which the fluorescent dye accumulating particles are dispersed are acquired, and data for the respective images are transmitted to the image processing device 2A.

Figure 3:
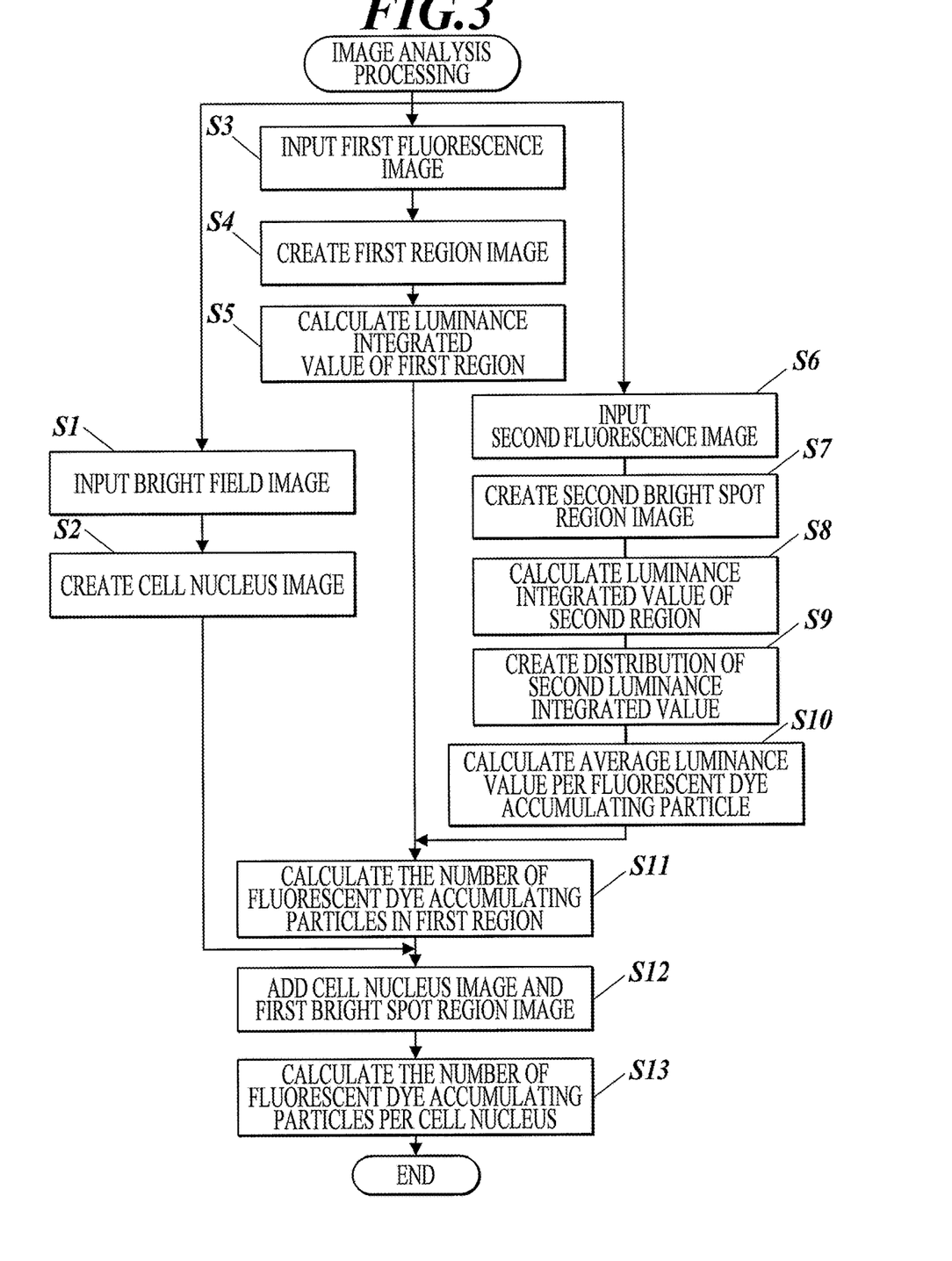
FIG. 3 is a flow chart indicating image analysis processing exerted by the control unit in FIG. 2.

FIG. 3 shows a flow chart of an image analysis processing in the image processing device 2A. The image analysis processing shown in FIG. 3 is exerted by cooperation of the control unit 21 and a program stored in the storage unit 25.

When the bright field image is inputted from the microscopic image acquiring device 1A by the communication I/F 24 (Step S1), a cell nucleus image in which a region of the cell nucleus is extracted from the bright field image is created (Step S2). In Step S2, the extraction may be performed by using any known methods, and any region, without being limited to the cell nucleus, may be extracted as a region of interest (ROI).

When the first fluorescence image is inputted from the microscopic image acquiring device 1A by the communication I/F 24 (Step S3: (first) input step), a first region image in which a certain region (hereinafter, referred to as a first region) is extracted from the first fluorescence image is created by the control unit 21 (Step S4). The certain region is any region of interest, and for example, a bright spot region. Next, a luminance value for (each) first region (first luminance integrated value) is calculated (Step S5: first luminance calculation step).

The processings of Steps S4 to S5 can be measured using any known methods, such as an open analytical software, ImageJ, and an automatic measuring software for all bright spots manufactured by G-Angstrom Co., Ltd., G-Count.

Figure 4A:
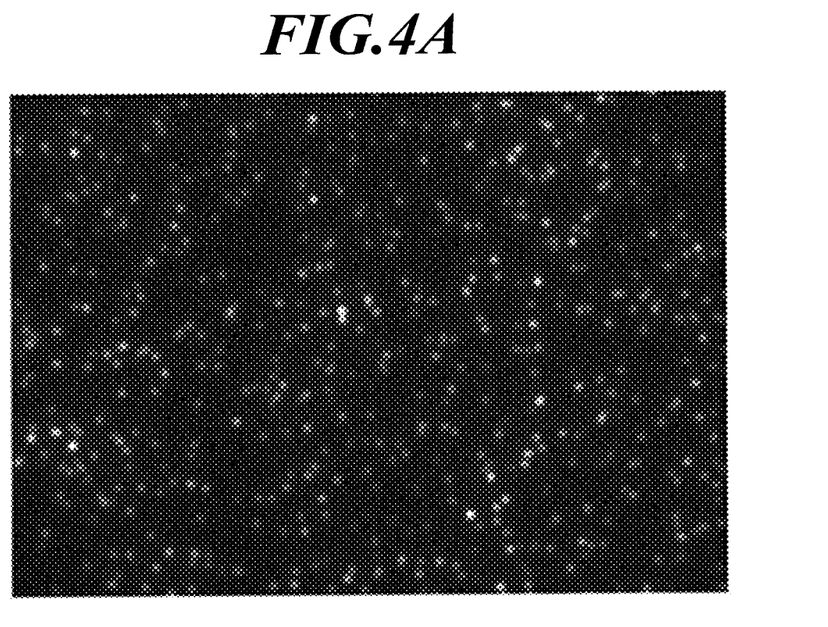
FIG. 4A shows an example of a second fluorescence image.
Figure 4B:
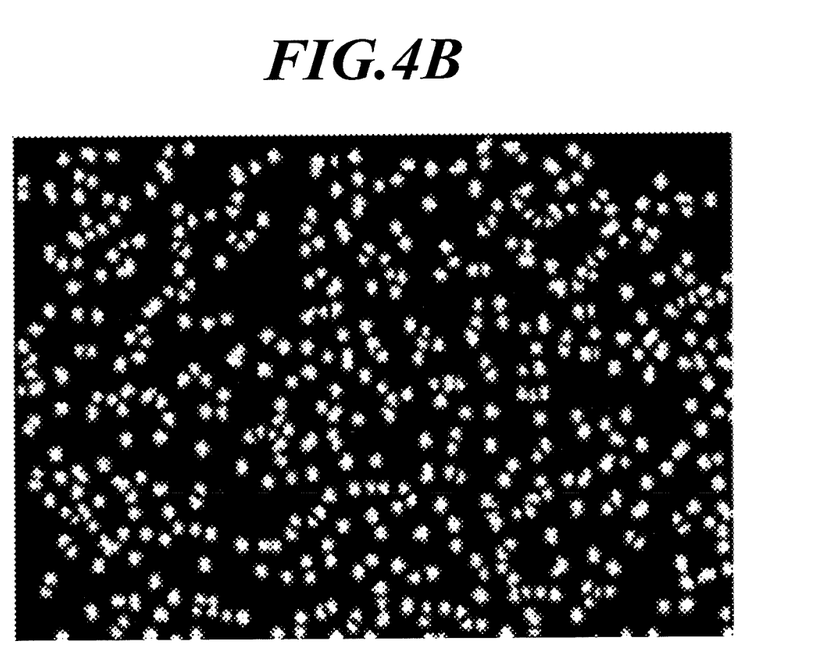
FIG. 4B shows an example of an image of a second bright spot region image.

When the second fluorescence image (FIG. 4A) is inputted from the microscopic image acquiring device 1A by the communication I/F 24 (Step S6: second input step), a second bright spot region image (FIG. 4B) in which bright spot region(s) (hereinafter, referred to as second region(s)), which indicate emission of light by the fluorescent dye accumulating particles, are extracted from the second fluorescence image is created by the control unit 21 (Step S7), and luminance integrated value(s) for the second region(s) (second luminance integrated value(s)) are calculated (Step S8: second luminance calculation step). The processings of Steps S7 to S8 can be measured using any known methods in the same manner as in Steps S4 to S5.

Figure 5:
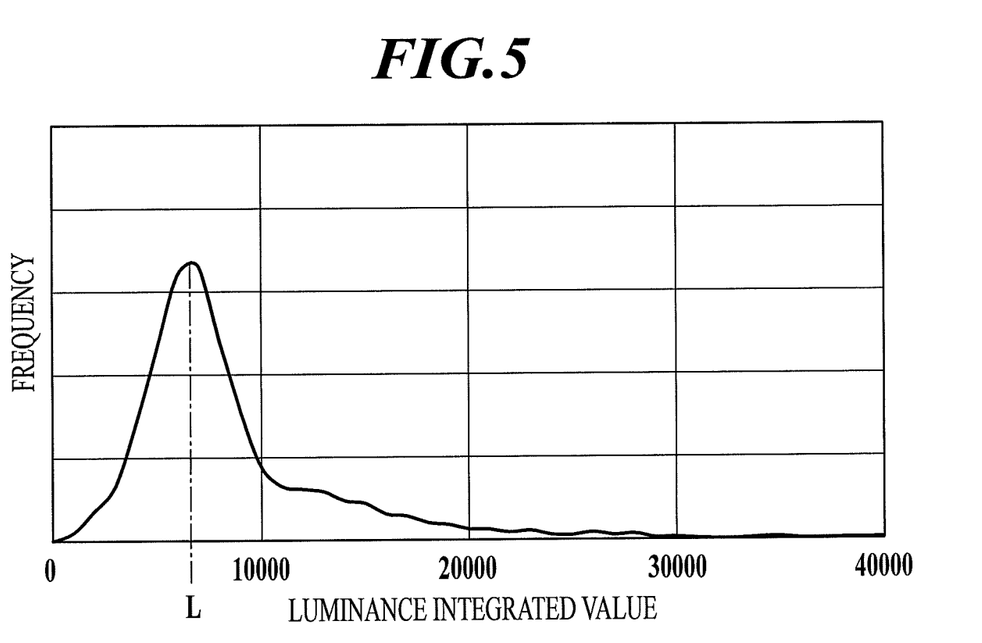
FIG. 5 is an example of a luminance distribution curve.

Next, a figure showing a distribution of the second luminance integrated values is created (Step S9). FIG. 5 shows an example of a luminance distribution curve with the horizontal axis of the luminance integrated values for the second regions and with the vertical axis of the frequency of the second luminance integrated values. Note that a histogram showing the frequency of the second luminance integrated values may be created in Step S9.

Based on the distribution of the second luminance integrated values, an average luminance value per fluorescent dye accumulating particle is calculated (Step S10: average luminance calculation step). In particular, a second luminance integrated value to be the mode (a luminance integrated value L at the peak of the luminance distribution curve, see FIG. 5) is calculated as the average luminance value.

From a viewpoint of enhancing the accuracy of the calculated average luminance value, it is preferable that the second luminance integrated values be calculated from 10000 or more second regions in Step S8 (second luminance calculation step) and that the average luminance value be calculated based on their distribution.

In addition, for the calculation of the mode, it is preferable that fitting or interpolation be performed to the distribution of the second luminance integrated values and that a luminance integrated value at the peak of the fitting curve or the interpolation curve is used as the average luminance value. The distribution of the second luminance integrated values of the present invention can be suitably fitted to, for example, a Gaussian curve, a quadratic curve, a Poisson distribution, a binomial distribution or the like.

In addition, when the fluorescent dye accumulating particles are dispersed without agglomerating onto the preparation onto which the fluorescent dye accumulating particles are dispersed, variation in areas of the second regions (coefficient of variation) is believed to be small, and therefore, it is preferable that the following Formula (1) with relation to areas of the second regions be satisfied:

$$0 \leq S\sigma/S_{ave} < 1.0, \quad \text{Formula (1):}$$

wherein $S\sigma$ represents a standard deviation of areas of the second regions and $S_{ave}$ represents an average value of areas of second regions.

When the coefficient of variation is 1 or more in Formula (1), many agglomerated, fluorescent dye accumulating particles are likely to be present on the preparation.

In addition, when a ratio between the area calculated from the average particle size of the fluorescent dye accumulating particles and the average area of the second regions is within a certain range, the fluorescent dye accumulating particles are believed to be dispersed without agglomerating, and therefore, it is preferable that the following Formula (2) with relation to areas of the second regions be satisfied:

$$0.10 < S_{ave} \cdot \pi (R_{ave}/2+\Delta)^2 < 10.00, \quad \text{Formula (2):}$$

wherein $S_{ave}$ represents the average area of the second regions, $R_{ave}$ represents the average particle size of the fluorescent dye accumulating particles, and $\Delta$ represents a resolution of an instrument that captures the fluorescence images.

When a value of the ratio is 10 or more in Formula (2), the average area of the extracted second regions is likely to be large, and many agglomerated, fluorescent dye accumulating particles are likely to be present on the preparation.

After finishing the processings of Step S5 and Step S10, the number of the fluorescent dye accumulating particles included in the first region is calculated from the first luminance integrated value and the average luminance value per fluorescent dye accumulating particle (Step S11: a particle count calculation step). In particular, for example, a value obtained by dividing the first luminance integrated value with the average luminance value is the number of the fluorescent dye accumulating particles.

Note that the processings of Step S6 to S10 are not necessarily performed every time the image processing is performed, and data of the average luminance value previously calculated may be used.

After finishing the processings of Step S2 and S11, an addition processing of the cell nucleus image and the first region image is performed (Step S12) and the number of the fluorescent dye accumulating particles per cell nucleus is calculated (Step S13).

Modified Example 1 of Average Luminance Calculation Step (Step S10)

Figure 6A:
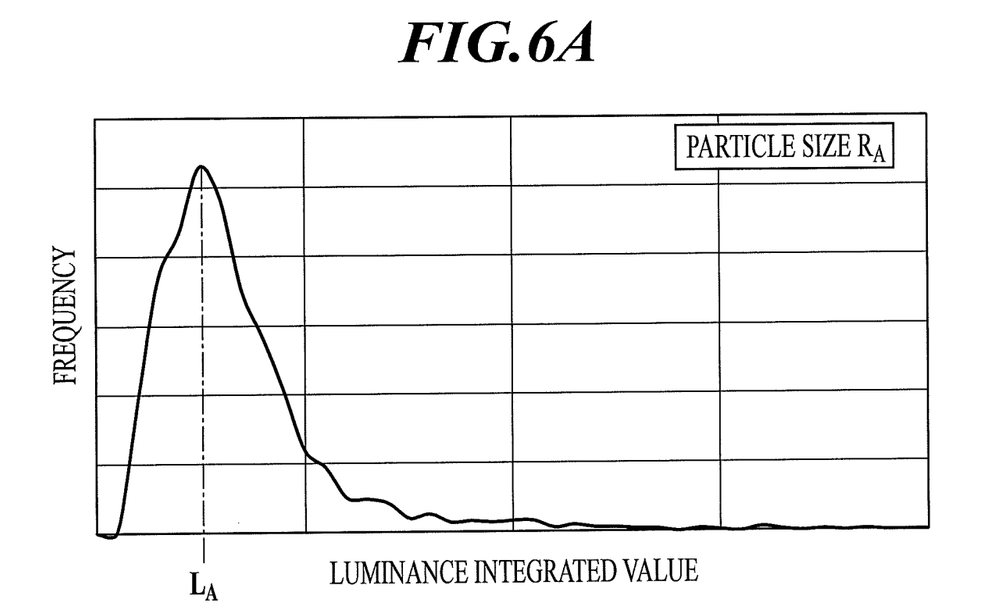
FIG. 6A is an example of a luminance distribution curve of fluorescent dye accumulating particles A with an average particle size of $R_A$.
Figure 6B:
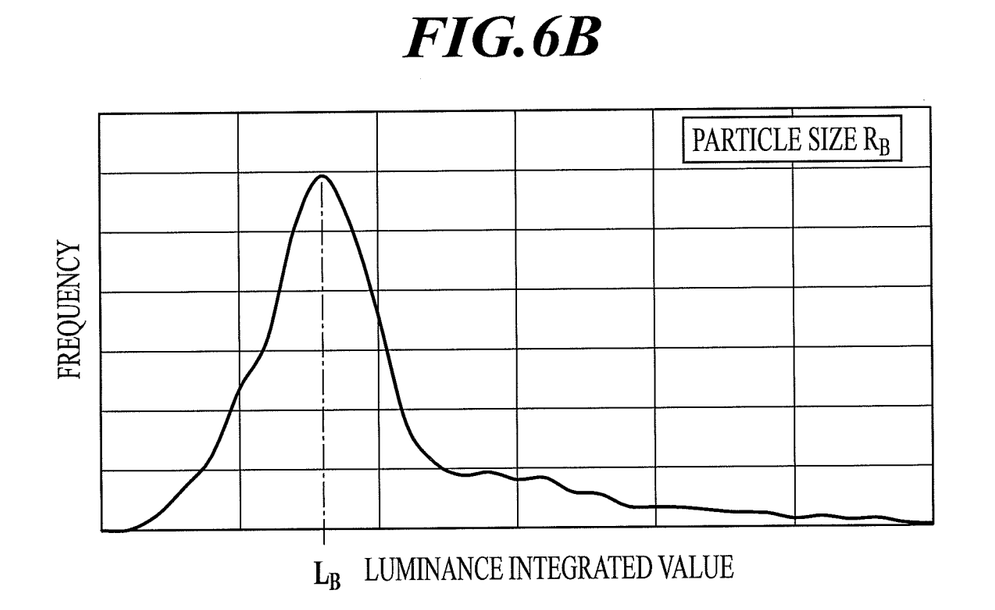
FIG. 6B is an example of a luminance distribution curve of fluorescent dye accumulating particles B with an average particle size of $R_B$.

FIG. 6A and FIG. 6B show luminance distribution curves created by using a fluorescent dye accumulating particle-dispersed preparation onto which fluorescent dye accumulating particles A with an average particle size of $R_A$ and fluorescent dye accumulating particles B with an average particle size of $R_B$ are dispersed, respectively. However, $R_A$ is smaller than $R_B$, and the fluorescent dye accumulating particles A and B are produced such that characteristics other than the particle size are the same. In addition, conditions for creating the luminance distribution curve are the same.

When the characteristics of fluorescent dye accumulating particles are the same, other than the particle size, it is believed that those with a larger particle size has a greater content of the fluorescent dyes, and thus has a higher luminance value. That is, it is believed that the average luminance value per fluorescent material accumulating particle, i.e., the amount of the fluorescent dyes, is proportional to the volume of the particle (cube of the particle size).

Based on this, in the modified example 1 of the average luminance calculation step, a lookup table or an interpolation curve showing the relationship between the average particle sizes $R_A$ and $R_B$ of the fluorescent dye accumulating particles A and B, and their average luminance values $L_A$ and $L_B$ (see FIG. 6A and FIG. 6B), respectively, is created, and is used to calculate an average luminance value $L_x$ of fluorescent dye accumulating particles X with a given average particle size $R_x$.

Note that two types of fluorescent dye accumulating particles with average particle sizes different from each other are described by way of example, but a more accurate average luminance value can be calculated when further more types are used.

Modified Example 2 of Average Luminance Calculation Step (Step S10)

Figure 7A:
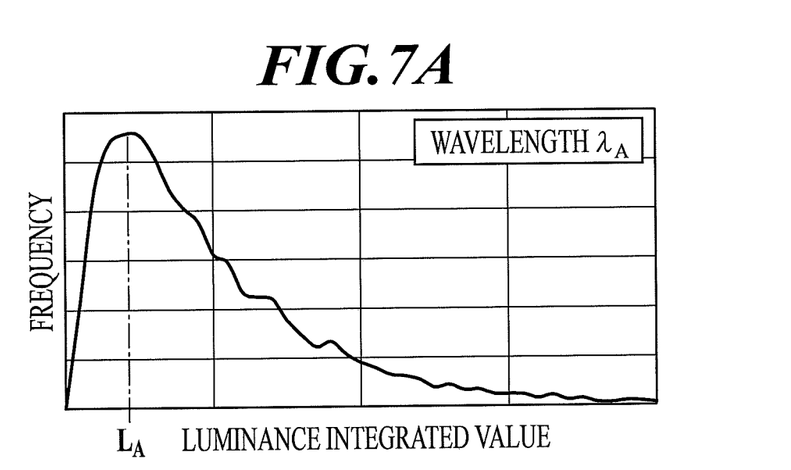
FIG. 7A is an example of a luminance distribution curve of fluorescent dye accumulating particles A with an emission wavelength of $\lambda_A$.
Figure 7B:
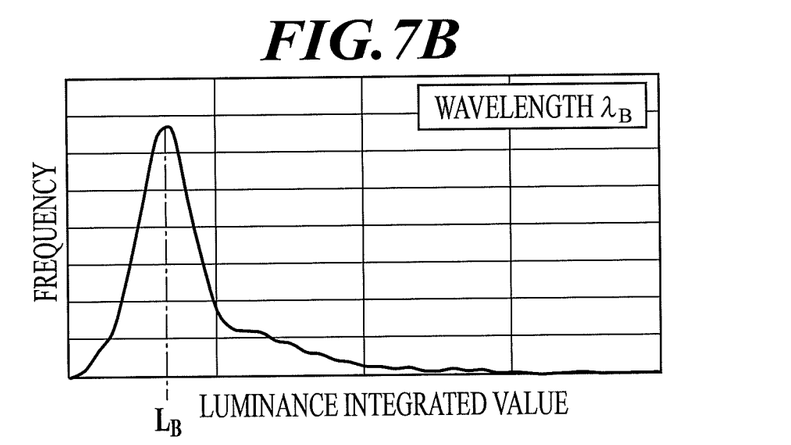
FIG. 7B is an example of a luminance distribution curve of fluorescent dye accumulating particles B with an emission wavelength of $\lambda_B$.
Figure 7C:
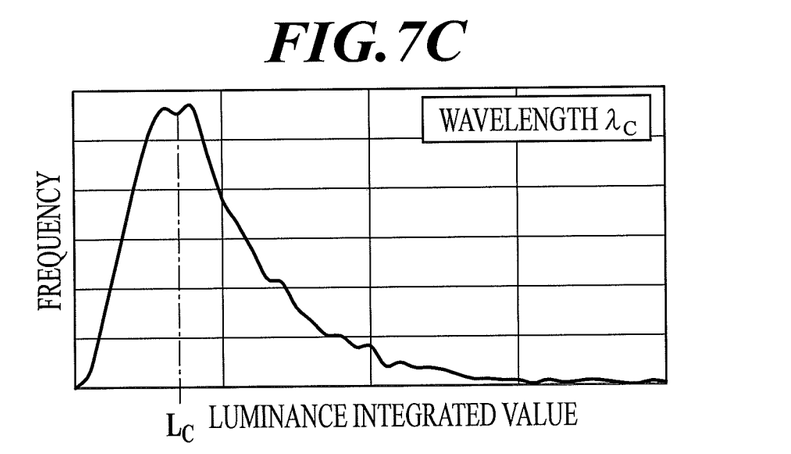
FIG. 7C is an example of a luminance distribution curve of fluorescent dye accumulating particles C with an emission wavelength of $\lambda_C$.

FIG. 7A to FIG. 7C show luminance distribution curves created based on fluorescent dye accumulating particle-dispersed preparations of fluorescent dye accumulating particles A, B and C with the peaks of the emission wavelength of $\lambda_A$, $\lambda_B$ and $\lambda_C$, respectively. Note that values of $\lambda_A$, $\lambda_B$ and $\lambda_C$ are different from each other.

In the modified example 2 of the average luminance calculation step, a lookup table or an interpolation curve showing the relationship between the emission wavelengths $\lambda_A$, $\lambda_B$ and $\lambda_C$ of the fluorescent dye accumulating particles A, B and C, and their average luminance values $L_A$, $L_B$ and $L_C$ (see FIG. 7A to FIG. 7C), respectively, is created, and is used to calculate an average luminance value $L_x$ of fluorescent dye accumulating particles X with a given wavelength $\lambda_x$. In the modified example 2, it is preferable that the lookup table or the interpolation curve be created after calibrating the average luminance values $L_A$, $L_B$ and $L_C$ in consideration of the spectrum and strength of the excitation light, properties of the filter or camera used for acquiring images, the type and amount of the fluorescent material included in the fluorescent dye accumulating particles, etc.

Note that three types of fluorescent dye accumulating particles with different fluorescence wavelengths are described by way of example, but the number of types may be two, or a more accurate average luminance value can be calculated when further more types are used.

Note that in the calibration step described above, it is preferable that the average luminance value per particle be capable of being calibrated when emission property (for example, luminance) of the fluorescent dye accumulating particles changes. Variation in the luminance value of the fluorescent dye accumulating particles can occur due to changes over time in the strength or wavelength property of the excitation light, or properties of the filter or camera used for acquiring images. In the calibration step, the presence or absence of the change in the luminance value is examined by measuring the luminance value of a standard sample with a constant emission property, and when a change is present, calibration is performed depending on the amount of change.

According to the embodiments of the present invention described above, calculation of the number of particles from the fluorescence image, rather than the number of bright spots, is easy based on the average luminance value per fluorescent dye accumulating particle. Accordingly, evaluation accuracy can be improved.

Moreover, the preparation onto which the fluorescent dye accumulating particles are dispersed without agglomerating is used, and therefore, a possibility of regarding, as one particle, a cluster in which the fluorescent dye accumulating particles are agglomerated as seen in the tissue section and the like is reduced. In addition, images with less noises (autofluorescence of cells, etc.) can be acquired. Accordingly, a more accurate average luminance value can be calculated.

Furthermore, by using the fluorescent dye accumulating particle-dispersed preparation, images in which the fluorescent dye accumulating particles are uniformly dispersed without agglomerating in the entire field of view can be obtained. Accordingly, a sufficient number of data can be acquired in an easier way compared to the case where fluorescent dye accumulating particles attaching to the tissue specimen are utilized.

In addition, in fluorescence images of the tissue specimen, well focused fluorescent dye accumulating particles and not focused fluorescent dye accumulating particles coexist due to the thickness of the specimen (cells) and attaching positions of the fluorescent dye accumulating particles. However, in the fluorescent dye accumulating particle-dispersed preparation of the present invention, the fluorescent dye accumulating particles are directly attached to the slide glass, thereby making the focusing easier.

Note that the contents described in the above embodiments is a suitable example of the present invention, and the present invention is not limited thereto.

In addition, in the above description, examples of using HDD, a semiconductor nonvolatile memory or the like as a computer readable medium for the program according to the present invention have been disclosed, but the medium is not limited to these examples. For other computer readable media, it is possible to apply a portable recording medium, such as CD-ROM. Moreover, as a medium that provides data of the program according to the present invention via a communication line, a carrier wave may be applied.

Besides, a detailed configuration and a detailed operation of each device constituting the diagnosis support information generation system 100 can also be appropriately modified within a range that does not depart from the spirit of the present invention.

Although embodiments of the present invention have been described and illustrated in detail, the disclosed embodiments are made for purposes of illustration and example only and not limitation. The scope of the present invention should be interpreted by terms of the appended claims.

INDUSTRIAL APPLICABILITY

As described above, the present invention is suitable for providing a biological material quantifying method, an image processing device, a pathological diagnosis support system and program with which a specific biological material in a tissue specimen can be quantified accurately and simply by using fluorescent dye accumulating particles bound to the biological material.

REFERENCE SIGNS LIST

1A Microscopic image acquiring device
2A Image processing device
21 Control unit
22 Manipulation unit
23 Display unit
24 Communication I/F
25 Storage unit
26 Bus
3A Cable
100 Diagnosis support information generation system

The invention claimed is:
1. A biological material quantifying method of quantifying a specific biological material in a specimen that has been stained using fluorescent dye accumulating particles capable of binding to the specific biological material, the biological material quantifying method comprising:

an input step of inputting a first fluorescence image obtained by capturing an image of the specimen;

a luminance calculation step of extracting a certain region from the first fluorescence image and calculating a first luminance integrated value by integrating luminance values of the certain region; and a particle count calculation step of calculating the number of the fluorescent dye accumulating particles included in the certain region from the first luminance integrated value and an average luminance value per said fluorescent dye accumulating particle, wherein the average luminance value is calculated from a distribution of second luminance integrated values obtained by integrating luminance values for individual bright spot regions, which indicate emission of light by the fluorescent dye accumulating particles, in a second fluorescence image obtained by capturing an image of a preparation onto which the fluorescent dye accumulating particles are dispersed without agglomerating.

2. The biological material quantifying method according to claim 1, wherein a density of the fluorescent dye accumulating particles on the preparation is $10^6$ counts/mm$^2$ or less.

3. The biological material quantifying method according to claim 1, satisfying the following Formula (1):

$$0 \leq S\sigma/S_{ave} < 1.0, \quad \text{Formula (1):}$$

wherein $S\sigma$ represents a standard deviation of areas of the bright spot regions and $S_{ave}$ represents an average value of areas of the bright spot regions.

4. The biological material quantifying method according to claim 1, satisfying the following Formula (2):

$$0.10 < S_{ave} \cdot \pi(R_{ave}/2+\Delta)^2 < 10.00, \quad \text{Formula (2):}$$

wherein $S_{ave}$ represents an average value of areas of the bright spot regions, $R_{ave}$ represents an average particle size of the fluorescent dye accumulating particles, and $\Delta$ represents a resolution of an instrument that captures the fluorescence images.

5. The biological material quantifying method according to claim 1, wherein the average luminance value is calculated using 10,000 or more luminance values for the individual bright spot regions.

6. The biological material quantifying method according to claim 1, wherein an average particle size of the fluorescent dye accumulating particles is 20 to 200 nm.

7. The biological material quantifying method according to claim 1, wherein a coefficient of variation of a particle size of the fluorescent dye accumulating particles is 15% or less.

8. The biological material quantifying method according to claim 1, wherein the average luminance value is a mode of the second luminance integrated values.

9. The biological material quantifying method according to claim 1, wherein the average luminance value is a maximum luminance value in a fitting curve or an interpolation curve that is created by performing fitting or interpolation to the distribution of the second luminance integrated values.

10. The biological material quantifying method according to claim 1, wherein the average luminance value is an average luminance value of fluorescent dye accumulating particles with a given particle size, calculated by using a lookup table or an interpolation curve that is created from the distribution of the second luminance integrated values based on multiple types of fluorescent dye accumulating particles with different average particle sizes.

11. The biological material quantifying method according to claim 1, wherein the average luminance value is an average luminance value at a fluorescence wavelength of a given particle size, calculated by using a lookup table or an interpolation curve that is created from the distribution of the second luminance integrated values based on multiple types of fluorescent dye accumulating particles with different emission wavelengths.

12. The biological material quantifying method according to claim 1, comprising a calibration step of calibrating the average luminance value per particle when emission property of the fluorescent dye accumulating particles changes.

13. The biological material quantifying method according to claim 1, comprising a preparation production step of producing the preparation by dispersing the fluorescent dye accumulating particles and dissolvable particles onto a slide glass and then removing said particles by dissolution.

14. The biological material quantifying method according to claim 1, comprising a preparation production step of producing the preparation by dispersing the fluorescent dye accumulating particles onto a slide glass that has been subjected to patterning with a dissolvable resin and then removing said resin by dissolution.

15. An image processing device that quantifies a specific biological material in a specimen that has been stained using fluorescent dye accumulating particles capable of binding to the specific biological material, the image processing device comprising:

an input unit that inputs a first fluorescence image obtained by capturing an image of the specimen; and a hardware processor that extracts a certain region from the first fluorescence image, calculates a first luminance integrated value by integrating luminance values of the certain region, and calculates the number of the fluorescent dye accumulating particles included in the certain region from the first luminance integrated value and an average luminance value per said fluorescent dye accumulating particle, wherein the average luminance value is calculated from a distribution of second luminance integrated values obtained by integrating luminance values for individual bright spot regions, which indicate emission of light by the fluorescent dye accumulating particles, in a second fluorescence image obtained by capturing an image of a preparation onto which the fluorescent dye accumulating particles are dispersed without agglomerating.

16. A pathological diagnosis support system comprising:
the image processing device according to claim 15; and
an image acquiring device that acquires the first fluorescence image and the second fluorescence image.

17. A non-temporary, computer-readable recording medium that stores a program, the program causing a computer that quantifies a specific biological material in a specimen that has been stained using fluorescent dye accumulating particles capable of binding to the specific biological material to:

extract a certain region from a first fluorescence image obtained by capturing an image of the specimen; calculate a first luminance integrated value by integrating luminance values of the certain region; and calculate the number of the fluorescent dye accumulating particles included in the certain region from the first luminance integrated value and an average luminance value per said fluorescent dye accumulating particle, wherein the average luminance value is calculated from a distribution of second luminance integrated values obtained by integrating luminance values for individual bright spot regions, which indicate emission of light by the fluorescent dye accumulating particles, in a second fluorescence image obtained by capturing an image of a preparation onto which the fluorescent dye accumulating particles are dispersed without agglomerating.

* * * * *